(12) United States Patent
Tamura et al.

(10) Patent No.: US 7,171,863 B2
(45) Date of Patent: Feb. 6, 2007

(54) TRANSFER UNIT AND AUTOMATIC ANALYZING APPARATUS HAVING SUCH TRANSFER UNIT

(75) Inventors: Tomoaki Tamura, Mishima (JP); Takayuki Mizutani, Mishima (JP)

(73) Assignee: Olympus Corporation, Tokyo (JP)

( * ) Notice: Subject to any disclaimer, the term of this patent is extended or adjusted under 35 U.S.C. 154(b) by 328 days.

(21) Appl. No.: 10/241,264

(22) Filed: Sep. 11, 2002

(65) Prior Publication Data

US 2003/0049170 A1 Mar. 13, 2003

(30) Foreign Application Priority Data

Sep. 12, 2001 (JP) ............................. 2001-277235

(51) Int. Cl.
*B01L 3/02* (2006.01)
(52) U.S. Cl. ............................. 73/864.14; 73/864.13; 73/864.16; 422/99; 422/100; 422/101; 422/102; 436/180
(58) Field of Classification Search .................. 422/63, 422/99–102; 435/6; 73/864.13, 864.16, 73/864.14; 436/180
See application file for complete search history.

(56) References Cited

U.S. PATENT DOCUMENTS

| | | | |
|---|---|---|---|
| 5,417,123 A | 5/1995 | D'Autry | |
| 5,538,849 A * | 7/1996 | Uematsu et al. | ................ 435/6 |
| 5,698,450 A | 12/1997 | Ringrose et al. | |

FOREIGN PATENT DOCUMENTS

| | | |
|---|---|---|
| DE | 199 17 375 A1 | 11/2000 |
| EP | 0 590 730 A2 | 4/1994 |
| JP | 59-33212 | 8/1984 |
| JP | 6-18534 | 1/1994 |
| WO | WO 99/57561 | 11/1999 |

* cited by examiner

*Primary Examiner*—Jill Warden
*Assistant Examiner*—Jyoti Nagpaul
(74) *Attorney, Agent, or Firm*—Scully, Scott, Murphy & Presser PC

(57) ABSTRACT

A transfer unit for transferring members such as reaction vessels having an upper end opening or dispensing tips or the like includes at least one arm pivotally movable about a shaft and a holder mounted on the arm for detachably supporting the member to be transferred. The holder is provided with a rod portion having a distal end adapted to be fitted in the upper end opening of the member to be transferred, a rod holding portion slidably and elastically supporting the rod portion and a guide portion surrounding the rod portion thereabout and sliding along the axis of the rod portion to release the fitting of the member from the distal end of the rod portion. The guide portion is formed with at least two elongated apertures extending in parallel with the axis of the rod portion, and the rod portion is provided with protrusions fixed thereto and extending through the elongated apertures to regulate the movement of the guide portion. By applying such a transfer unit to a chemicobiological or immunity analyzing apparatus, the analyzing operation can be performed at a higher speed with a higher efficiency and a particularly compact analyzing apparatus is possible.

13 Claims, 14 Drawing Sheets

FIG. 7a
FIG. 7b
FIG. 7c
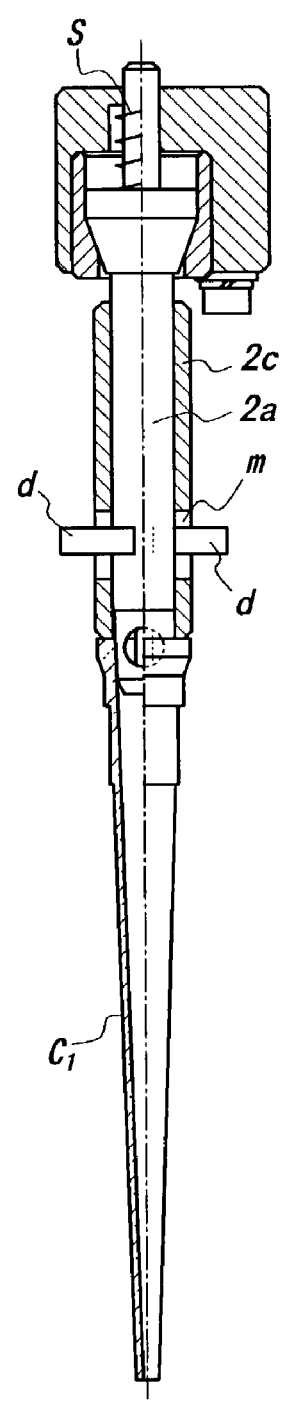
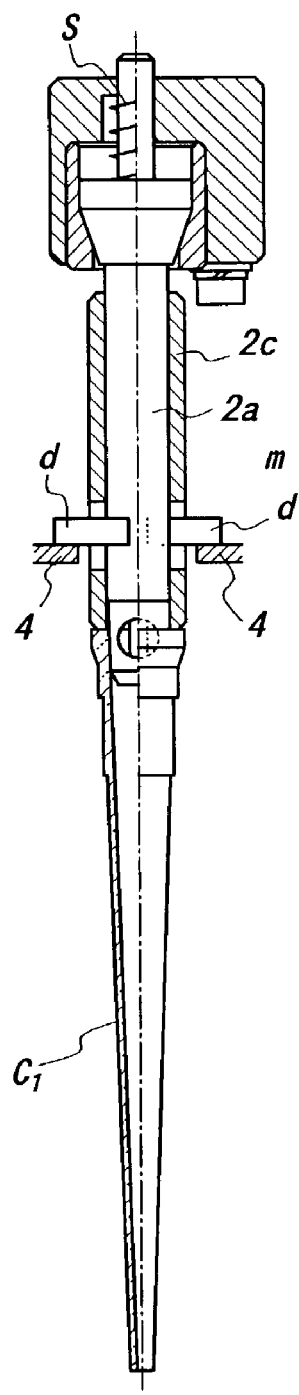
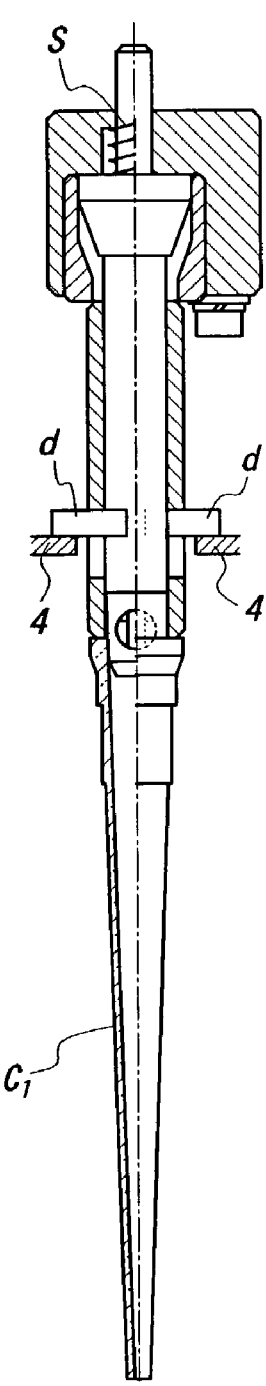

TRANSFER UNIT AND AUTOMATIC ANALYZING APPARATUS HAVING SUCH TRANSFER UNIT

BACKGROUND OF THE INVENTION

This invention relates to a transfer unit capable of transferring reaction vessels, dispensing tips and the like with a simple construction and more particularly to an automatic analyzing apparatus including such a transfer unit.

In the fields of the immunity analysis, chemicobiological analysis and the like, in recent years disposable dispensing tips and reaction vessels have been used in order to avoid errors in data due to carry-over and defective or failed washing. Such dispensing tips and reaction vessels are stored at particular locations and, as required, they are transferred by a transfer mechanism to predetermined positions (for example, dispensing tips after dispensation to discarding positions and reaction vessels to reaction tables or discarding positions) where the dispensing tips and reaction vessels are removed from the transfer mechanism.

On the other hand, recently there has been a strong need for the apparatuses of this kind to miniaturize and to reduce the manufacturing cost, and various attempts have been made to comply with these requirements. However, the miniaturization and low cost manufacture of the apparatuses have not been realized to a satisfactory extent because the transfer portion for tips and reaction vessels are imperative. Such prior art apparatuses have been disclosed in Japanese Patent Application Publication No. S59-33,212 and Japanese Patent Application Opened No. H6-18,534.

In the apparatus disclosed in the Japanese Patent Application Publication No. S59-33,212, recessed taking-off members are provided for mounting and dismounting tips, which may realize effective exchanging of tips. However, this apparatus suffers several disadvantages from the taking-off members required at all the mounting and dismounting locations, from complicated driving system due to three dimensional movements in longitudinal, transverse and vertical directions required in dismounting operations, and from spaces required to prevent the interference of the taking-off members with other mechanisms of the apparatus.

On the other hand, in the apparatus disclosed in the Japanese Patent Application Opened No. H6-18,534, removal of tips would be effected only by vertical movements to render the apparatus compact. With this apparatus, however, the complexity in construction of piping, rods, stoppers of rods, control mechanism for the stoppers and transfer mechanism has not been reduced or amended.

In general, robot arms have been known for gripping and transferring members such as reaction vessels, test tubes and the like. With such robot arms, however, the apparatus becomes bulky and control members such as driving motors or the like extremely increase, resulting in increased manufacturing cost which does not comply with the requirement in market.

In addition, with the apparatuses of this kind, it is desirable to detect or ascertain whether the tips or reaction vessels are securely held or removed in transferring operation. Incomplete holding and imperfect removal of these members will be caused by structural errors and operator's mishandling (has been forgotten to set tips or reaction vessels) and these incomplete holding and removal will in turn cause failure of the apparatus and incorrect data. In order to eliminate such difficulties, with the prior art apparatuses, light transmission sensors or image monitors are suitably arranged at particular positions to ascertain the holding and removal with the aid of light transmittance, reflectivity and image information. With such detecting means, however, particular spaces are needed for arranging the sensors, and arms must be once stopped or decelerated in the vicinity of the sensors so that detecting performance is deteriorated and time required for detection is increased.

SUMMARY OF THE INVENTION

It is an object of the invention to provide an improved transfer unit which overcomes all the disadvantages of the prior art and which is relatively simple in construction and hence compact in apparatus, inexpensive to manufacture and reliable in operation.

It is another object of the invention to provide an automatic analyzing apparatus provided with the above transfer unit, which also accomplishes the advantages to the fullest extent the same as those of the transfer unit according to the invention.

In order to achieve the first object, the transfer unit of the present invention includes at least one holder which transfer members to proceed a reaction in an automatic analyzer. The holder has a rod portion and a guide portion, one of which can slide relatively to the other elastically to release the fittings of the member from the distal end of the rod portion.

In a preferred embodiment of the present invention, the rod portion has at least one window at the top of the rod for detecting the fitting and removing of the member onto and from the rod portion.

In another preferred embodiment, the holder has a guide portion with at least two elongated apertures extending in parallel with the axis of the rod portion being provided with protrusion fixed thereto and extending through the elongated apertures of the guide portion.

In the present invention of the present invention, the members may be composed of a reaction vessels or dispersing tips.

In order to achieve the second object, the automatic analyzing apparatus of the present invention includes a reaction portion for causing a reaction of a substance and a reagent mixed into a liquid, a detecting portion for signal or reaction from the liquid, washing portion for removing an unreacted substance in the reacted liquids, and a transfer unit to transfer members to proceed a reaction.

In a preferred embodiment of the present invention, the transfer unit has at least one holder which transfer members to proceed a reaction in an automatic analyzer. The holder has a rod portion and a guide portion, one of which can slide relatively to the other elastically to release the fittings of the member from the distal end of the rod portion.

In another preferred embodiment of the present invention, the rod portion has at least one window at the top of the rod for detecting the fitting and removing of the member onto and from the rod portion.

In still another preferred embodiment of the present invention, the holder has a guide portion with at least two elongated apertures extending in parallel with the axis of the rod portion being provided with protrusion fixed thereto and extending through the elongated apertures of the guide portion.

The members may be composed of the reaction vessels or dispensing tips. Also, the washing portion may work for B/F separation.

The transfer unit comprises holders to make the transfer unit compact as a whole. The holder of the transfer unit comprises a rod portion, a rod holding portion and a guide portion. The rod portion is inserted into the upper end opening of the member being transferred to effect the mounting of the member, and the member is urged by the guide portion to remove the member from the rod portion.

The automatic analyzing apparatus is arranged in a device or in a single frame so as to permit the reaction, detecting and cleaning portions to be independently arranged to have respective ports, thereby reducing dead spaces in the apparatus to render the apparatus compact.

The reaction, detecting and cleaning portions are made in the form of turn tables to shorten the moving distances of nozzles used in dispensing samples and reagents and cleaning to the minimum distances, to simplify the control concerning with measurement, to improve accuracy and reliability and to reduce manufacturing cost. Moreover, transferring distances of reaction vessels between the tables become shorter, so that it is possible to improve the reliability and to reduce the manufacturing cost. The reaction time can be severely determined correspondingly to the movement of the tables, thereby improving the accuracy of measured data. In this case, the respective tables can be smaller, so that temperature control can be easily performed.

By previously providing a pretreatment port and a dilution port in reaction portion, the reaction portion can be smaller which would otherwise be bulky, thereby enabling application to pretreatment items that would otherwise be impossible.

Assuming that the apparatus is used in measurement of immunity items whose magnetic material is solidus carrier (magnetic particle carriers), there are provided a magnetically collecting function as a magnet for magnetically collecting the magnetic particle carriers, and an agitating function for dispersing the magnetic particle carriers. By making the cleaning portion independent, it is possible to gather members required in the case using for immunity items as magnetic particle carriers together into one. Such members are, for example, the magnets (magnets for magnetically collecting magnetic particle carriers), agitating function and cleaning nozzles, which would otherwise be plural after first reaction and after second reaction, respectively. Therefore, it serves to reduce the manufacturing cost. In this case, the number of nozzles to be used can be reduced so that difference in cleaning performance between nozzles separately produced can be smaller to improve the reliability of measured data.

Assuming that weak light-emission is detected at the detecting portion, a detecting measurement portion completely shut off from light is previously provided separately from the detecting reaction portion so that even weak light-emission reaction can be measured with high accuracy and high sensitivity, thereby enabling detection by fluorescence and chemical light-emission as well as the prior art colorimetric detection.

According to the invention the reaction vessels themselves are transferred between the respective portions. At that time, a monitoring function can be added for securely monitoring the transferring state of the reaction vessels. By transferring the reaction vessels themselves as described above, cleaning of nozzles for transferring liquids to be inspected and cleaning of reaction vessels after respective reactions (cleaning of reaction vessels after transferring of liquids to be inspected) can be dispensed with. Moreover, it is possible to prevent incorrect data due to insufficient cleaning and to reduce running cost by reducing the washing operation. Disposable reaction vessels can be used so that the contamination of reaction vessels that is not allowed in immunity analysis can be avoided, and the reduction of washing mechanism for reaction vessels serves to improve the reliability of data and to miniaturize the apparatus.

Means for detecting whether reaction vessels have been exactly transferred may be provided in the transfer mechanism. Such means do not affect the size of the apparatus.

According to the invention, the reaction, detecting and cleaning portions and reagent storing portion can be arranged on a locus through which a dispensing nozzle passes so that only one dispensing nozzle unit can be sufficiently used different from the prior art requiring a plurality of dispensing nozzle units.

According to the invention it is possible to transfer the disposable dispensing tips and reaction vessels securely with a simple mechanism, thereby realizing the miniaturization of the apparatus and reducing its manufacturing cost. By providing sensors on the holders of the transfer unit, the mounted and dismounted condition of the reaction vessels and the like can be always monitored to improve the reliability of the apparatus itself. According to the invention, moreover, the high-speed treatment and the miniaturization of the automatic analyzing apparatus itself can be simultaneously accomplished. The apparatus according to the invention is inexpensive, wieldy or easy to use and high in reliability and can provide reliable data.

The invention will be more fully understood by referring to the following detailed specification and claims taken in connection with the appended drawings.

BRIEF DESCRIPTION OF THE DRAWINGS

FIG. 1b is a side view of the transfer unit shown in FIG. 1a;

FIGS. 7a, 7b and 7c are views illustrating the mounting and dismounting steps of a dispensing tip according to the invention;

DESCRIPTION OF THE PREFERRED EMBODIMENTS

The present invention will be concretely explained in more detail with reference to the drawings hereinafter.

Figure 1A:
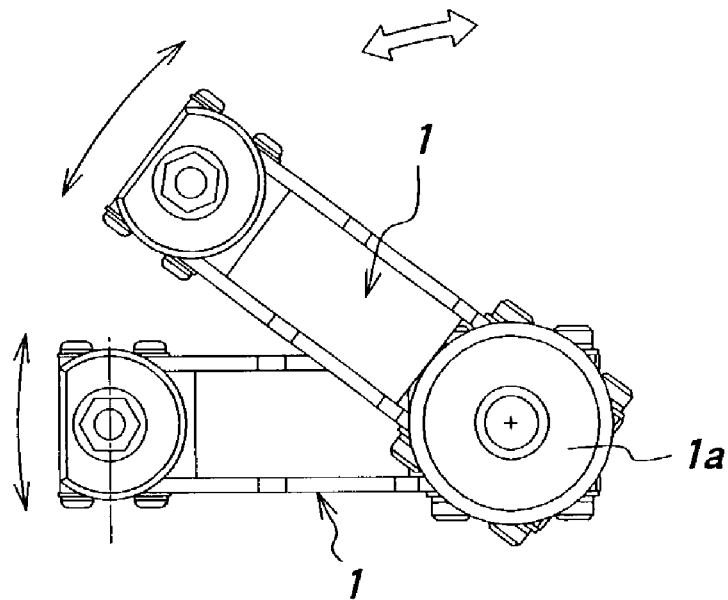
FIG. 1a is a plan view of a transfer unit according to the invention.
Figure 1B:
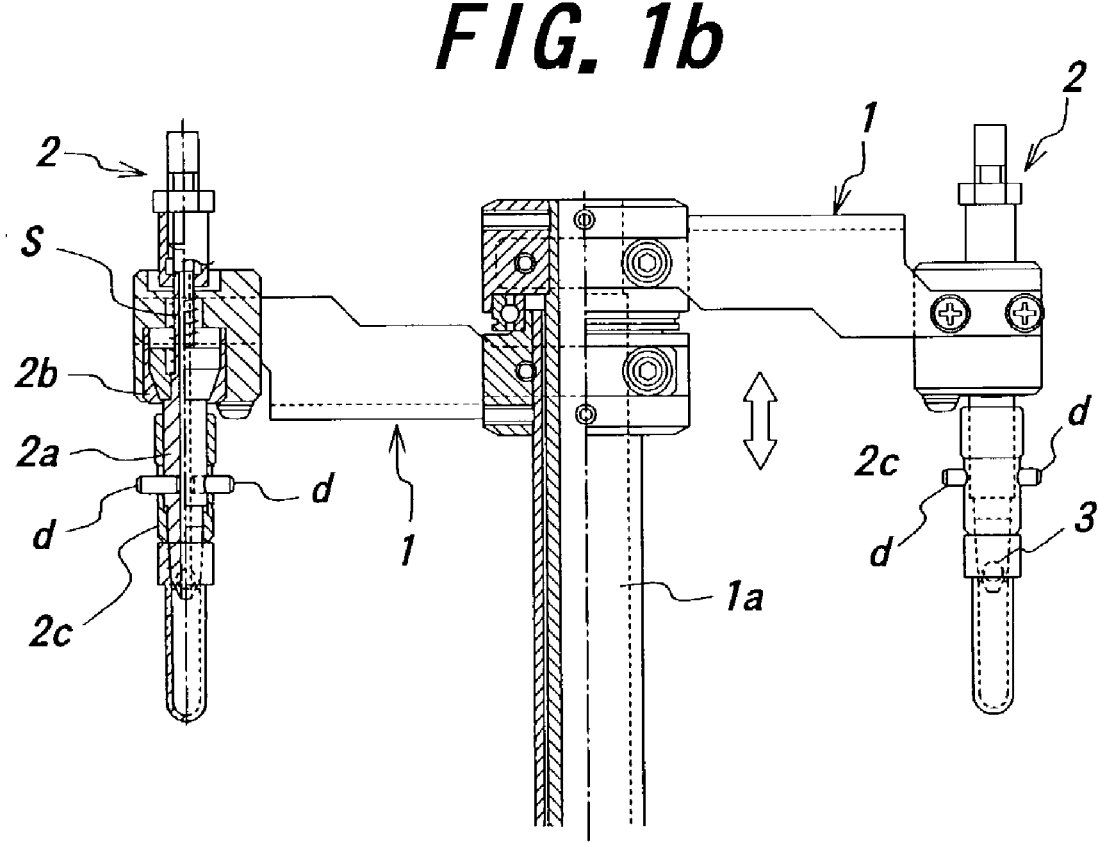
Figure 2:
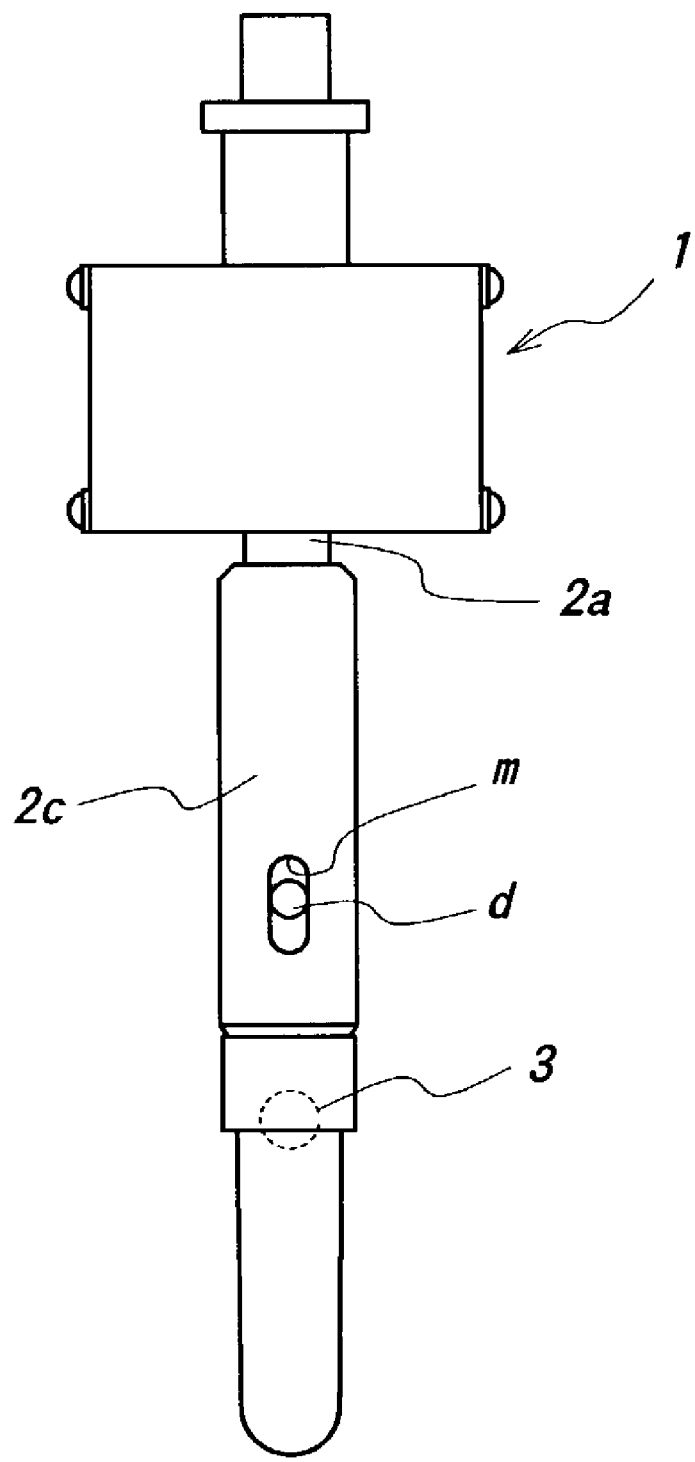
FIG. 2 is a view illustrating part of the transfer unit shown in FIG. 1b on an enlarged scale.

FIGS. 1a and 1b exemplarily illustrate a transfer unit which comprises arms 1 (two arms in the illustrated embodiment) and holders 2 mounted on the arms 1, respectively. The arms 1 themselves are pivotally supported by a shaft 1a so as to be pivotally moved around the shaft 1a.

Each of the holders 2 comprises a rod portion 2a, a rod holding portion 2b for holding the rod portion 2a in a slidably hung state, and a guide portion 2c surrounding and slidable along the rod portion 2a. The guide portion 2c is formed with at least two elongated apertures m extending in the axial direction of the rod portion 2a. On the other hand, the rod portion 2a is provided with protrusions d fixed thereto extending through the elongated apertures m for limiting the movement of the guide portion 2c.

Moreover, the rod portion 2a is provided at forward or distal end with windows (two windows may be provided) and is further formed in its interior with a passage leading to a pump to be used in fractional dispensing (this passage is not needed when used only in transferring reaction vessels or reactors), and a further passage for arranging therein optical sensors such as optical fibers. In this manner, the mounting and dismounting of reactin vessels are monitored with the aid of detection of reflected light of the light emitted from the optical sensors at the windows 3.

The rod holding portion 2b has an inner cavity that is downward tapered, while the rod portion 2a has an outer configuration commensurate with the downward tapered cavity of the rod holding portion 2b, thereby facilitating the centering between the rod holding portion 2b and the rod portion 2a. The rod portion 2a is elastically supported and invariably urged downward by an elastic member s (for example, a spring or the like) arranged between the rod portion 2a and the arm 1.

Figure 3:
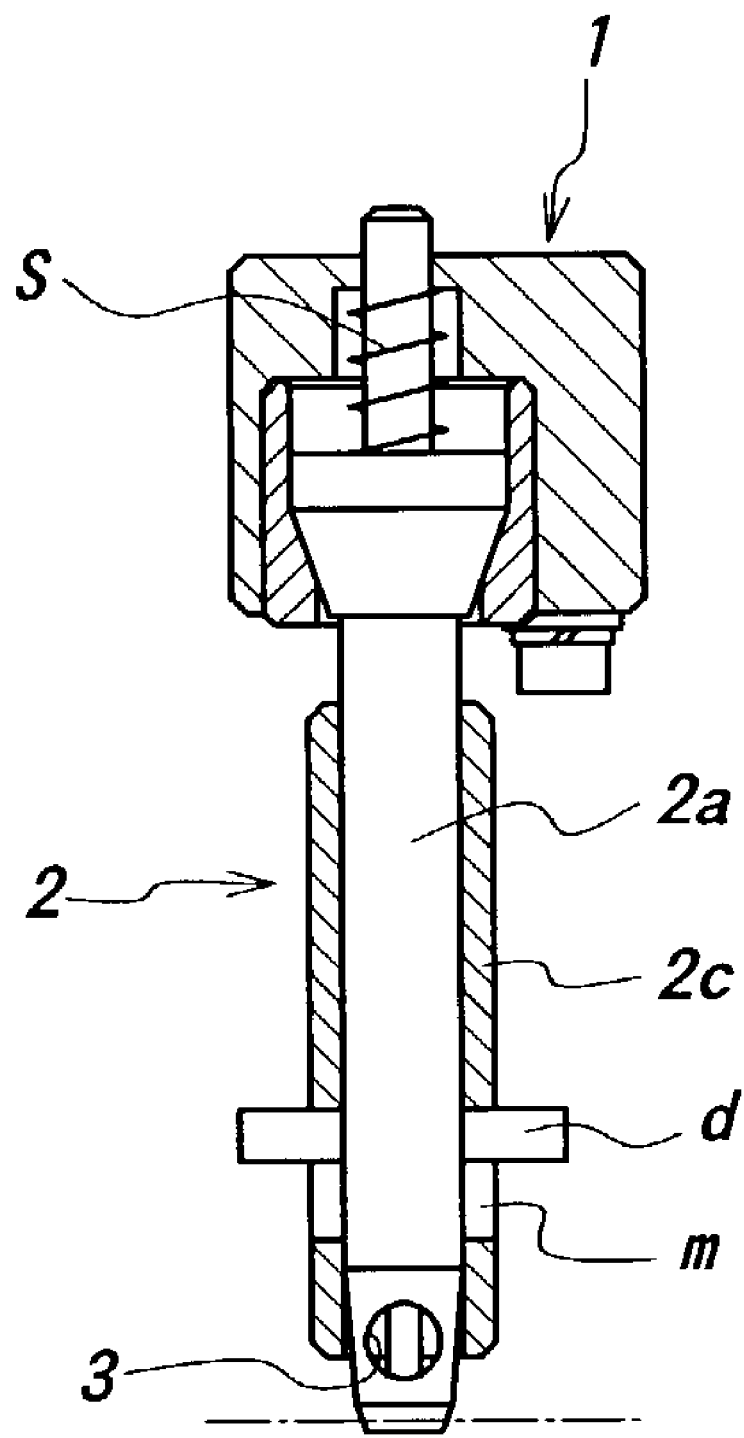
FIG. 3 is a view illustrating an important portion of the transfer unit according to the invention on an enlarged scale.
Figure 4:
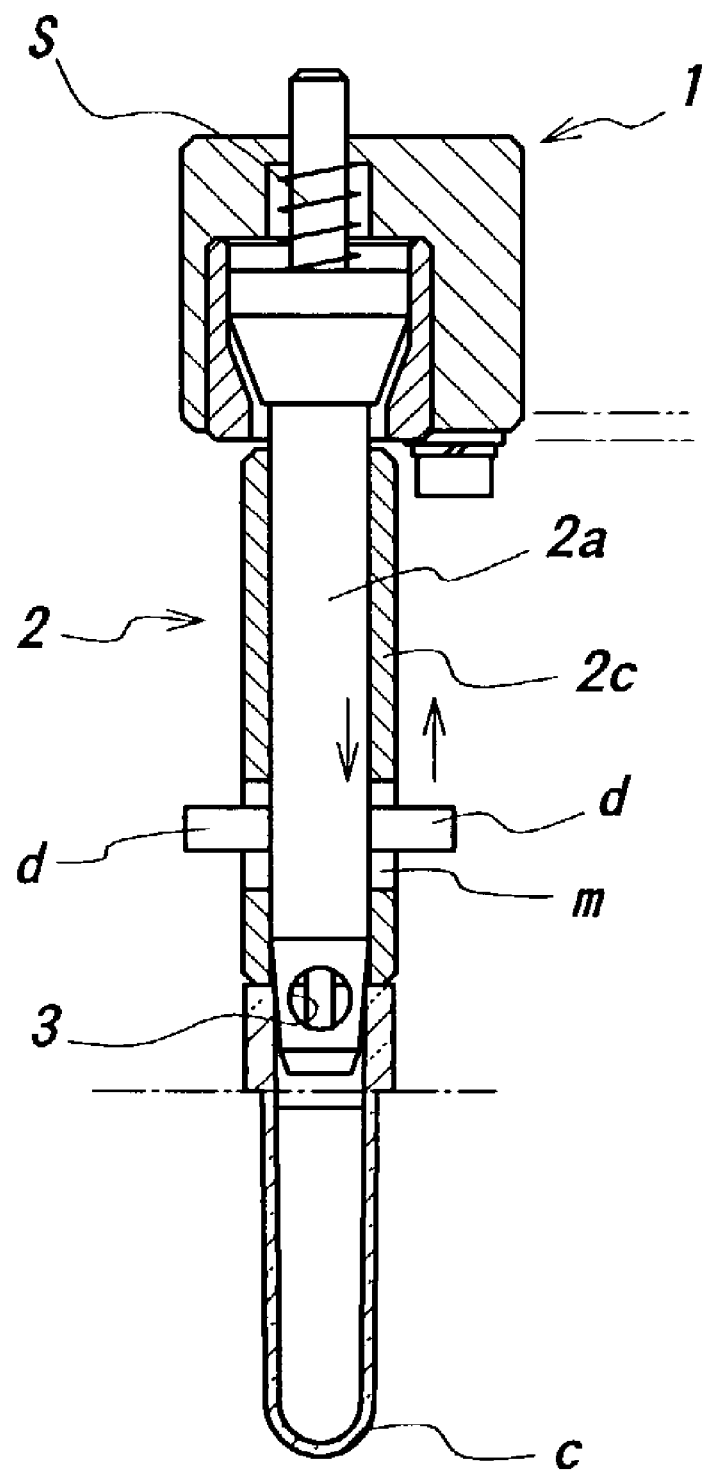
FIG. 4 is a view for explaining the mounting of a reactor vessel on the transfer unit according to the invention.

FIG. 3 illustrates the holder 2 before a reaction vessel or reactor is mounted thereon. The shaft 1a is lowered together with the arm 1 by means of a lifting mechanism (not shown) previously provided on the shaft 1a so that the lower end of the rod portion 2a is forced into the upper opening of a reaction vessel c as a member to be transferred as shown in FIG. 4. In this manner, the reaction vessel c is mounted on the holder 2.

At this moment, the guide portion 2c will slide upward within the range determined by the elongated apertures, thereby preventing any interference of the guide portion 2c with the fitting of the reaction vessel. Moreover, the elastic member s affords an optimum urging force required to ensure the fitting of the reaction vessel, thereby avoiding any failure caused in the fitting of the reaction vessel and preventing the tips and reaction vessels from being damaged. (It is desirable to adjust the elastic member previously to permit its contraction allowance to become of the order of 3 mm.)

Figure 5:
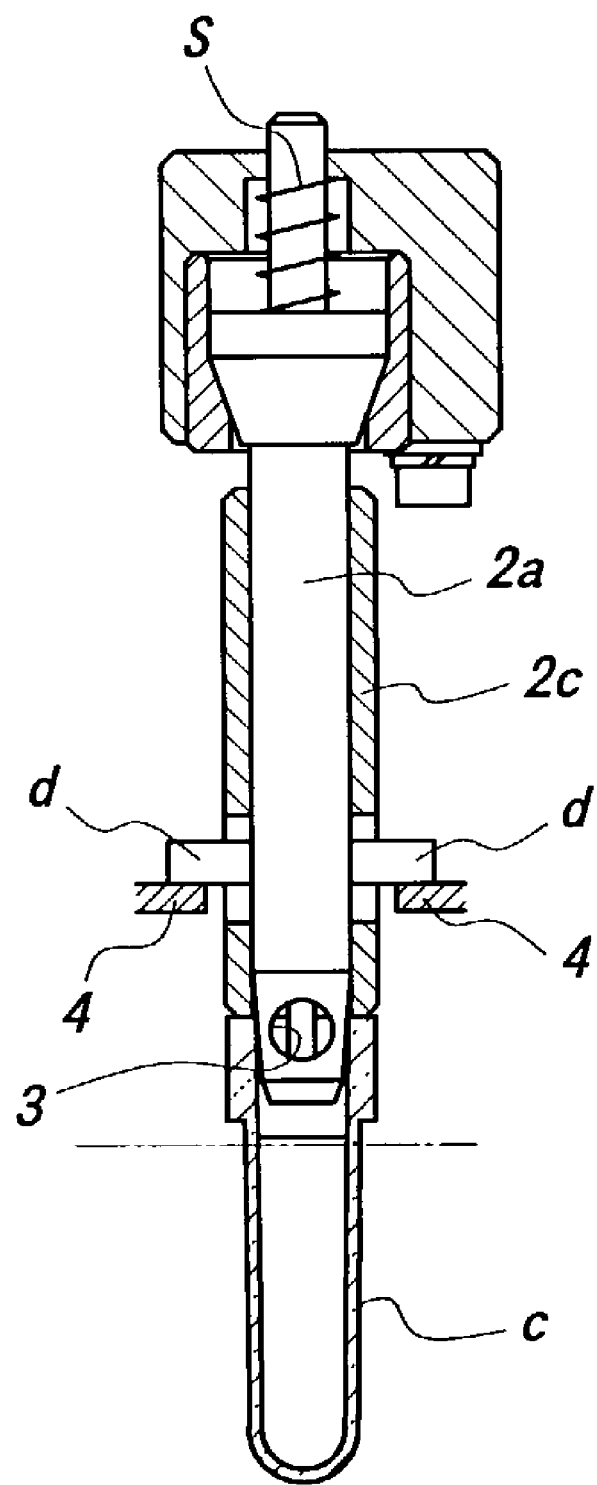
FIG. 5 is a view for explaining the dismounting of the reactor vessel on the transfer unit according to the invention.
Figure 6:
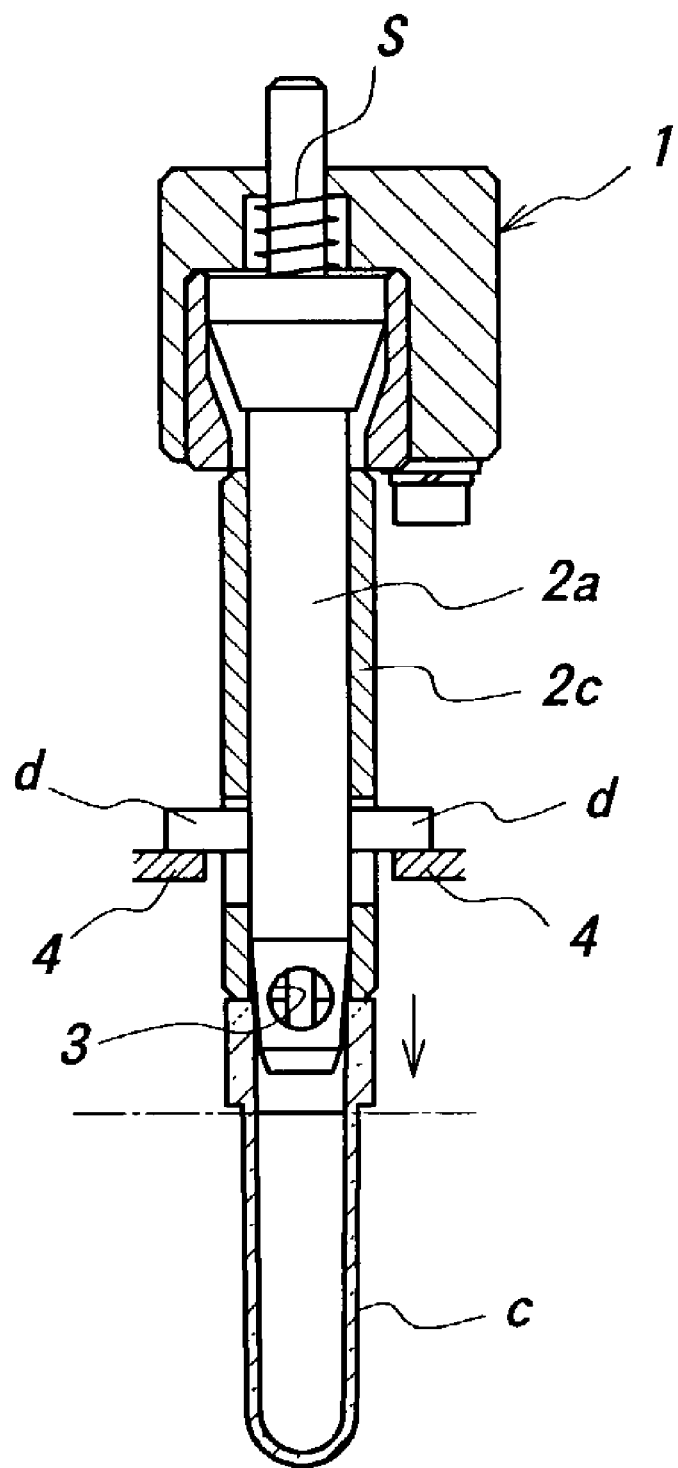
FIG. 6 is a view illustrating another step of the dismounting of the reaction vessel.

The reaction vessel c attached to the holder 2 is transferred to a predetermined position by a pivotal movement of the arm 1. In order to remove the reaction vessel c from the holder 2, the protrusions d provided on the rod portion 2a are brought into contact with a fixed member 4 (for example, a cover for the reaction table, tubes for discarding used reaction vessels or the like) to fix the position of the rod portion 2a as shown in FIG. 5 and further the arm 1 is lowered downward through a distance corresponding to a permissible value of contraction of the elastic member s as shown in FIG. 6. (It is desirable to adjust the elastic member previously to permit its contraction allowance to become of the order of 5 mm.) As a result, the rod holding portion 2b urges only the reaction vessel c downward through the guide portion 2c to remove the reaction vessel c from the rod portion 2a.

A light is irradiated from an optical sensor through the window 3 provided at the lower end of the rod portion 2a. In mounting and dismounting reaction vessels c, by comparing the light with a reference value previously set, an operator can ascertain whether the reaction vessel has been fitted with the rod portion (including whether it has been snugly fitted, or whether there is a possibility of leakage) or whether the reaction vessel has been removed.

While the arms 1 are shown to be pivotally movable about the shaft 1a in the illustrated embodiment, it will be apparent that the arms may be movable vertically and horizontally with the aid of linear guide means. The present invention should not be limited to the specific features.

Figure 8:
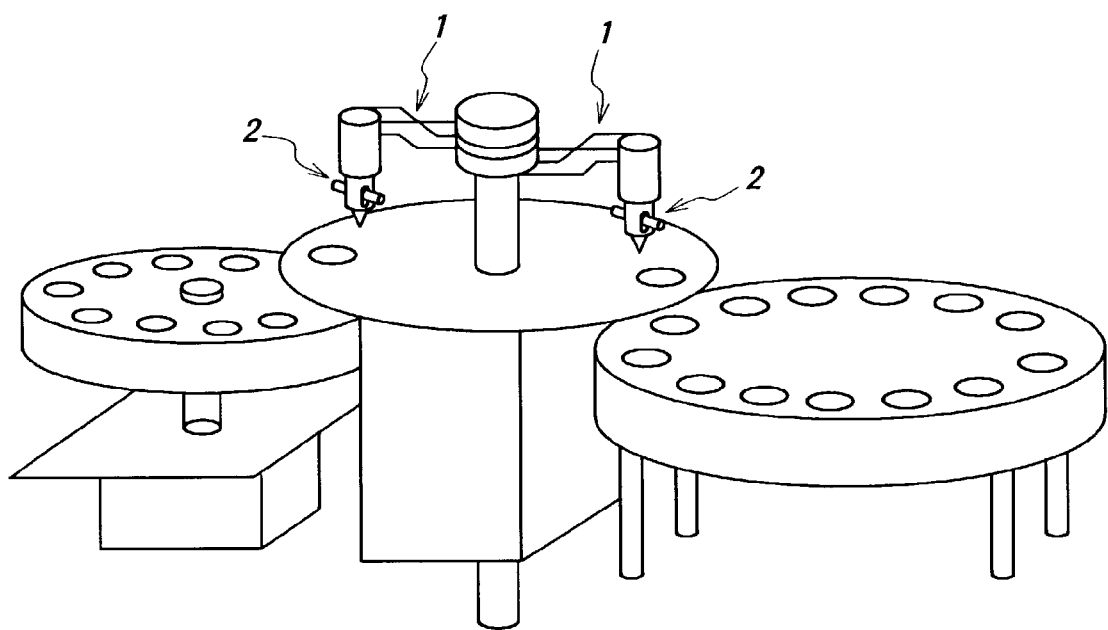
FIG. 8 is a perspective view illustrating the outline of the transfer unit according to the invention.

FIGS. 7a to 7c illustrate relations between the dispensing tips $c_1$ and the holder 2 before and after they are fitted with each other. FIG. 8 shows the outline of the transfer unit in a pictorial view. A dispensing tip $c_1$ can be mounted and dismounted in the same manner as in the reaction vessel c described above.

By employing the arrangement described above, it becomes capable not only of miniaturizing the transfer unit but also reducing the manufacturing cost and improving reliability concerning the transference. Such a transfer unit is applicable to the transference of dispensing tips $c_1$, in addition to reaction vessels c. Objects to be transferred should not be limited to particular ones.

Figure 9:
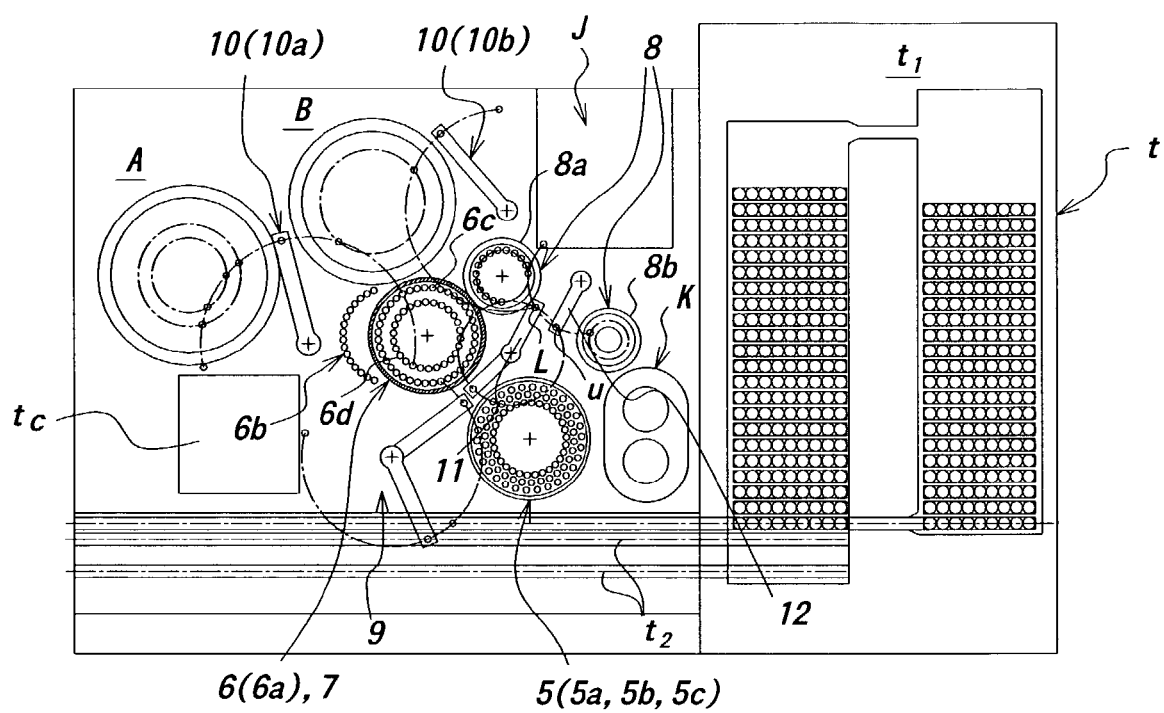
FIG. 9 is a view illustrating the entire construction of the automatic analyzing apparatus provided with the transfer unit according to the invention.
Figure 10:
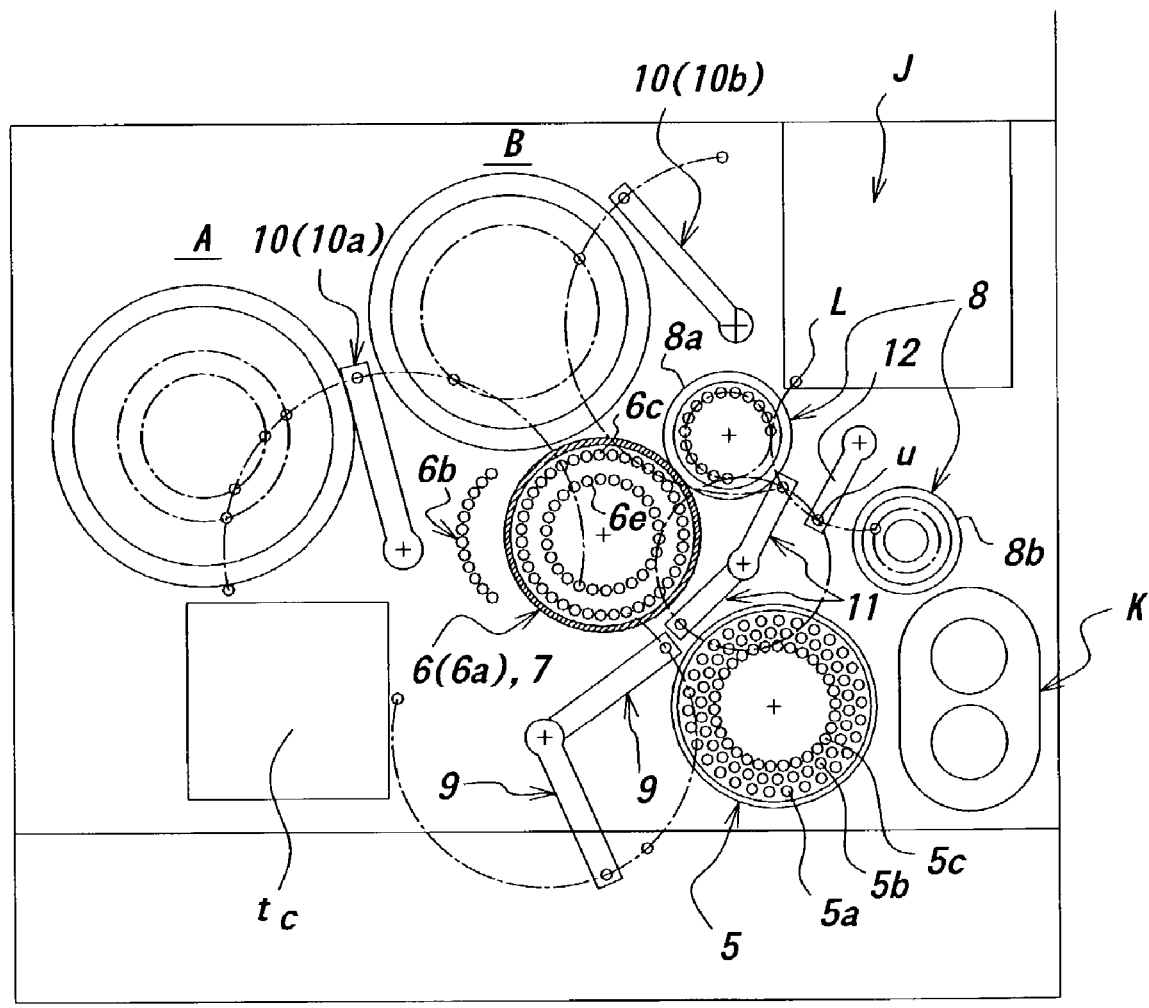
FIG. 10 is a view illustrating an important part (analyzer) of the apparatus shown in FIG. 9.

FIG. 9 illustrates the entire construction of an automatic analyzing apparatus for immunity measurement based on chemical light-emission detection using magnetic particle carriers as solidus carriers, to which the automatic analyzing apparatus according to the invention is applied. FIG. 10 shows an important part of the apparatus shown in FIG. 9.

In FIGS. 9 and 10, the automatic analyzing apparatus comprises a immunity reaction portion (referred to hereinafter as "immunity reaction table") 5, which may have a configuration of triple construction dividing its reaction line into outer, intermediate and inner circumferential lines 5a, 5b and 5c. The outer circumferential line 5a is used for pretreatment and predilution (which means such a dilution to be previously performed preparatory to a next step) and the intermediate circumferential line 5b for immunity reaction between samples and solidus carrier reagents. The inner circumferential line 5c is for immunity reaction between sample-solidus carrier immunity composite material and marker reagent combined with marker substance for producing signals.

The automatic analyzing apparatus further comprises a cleaning portion (referred to hereinafter as "BF table") 6 which has a magnetically collecting mechanism (magnet) 6a for magnetically collecting magnetic particle carriers required for BF (bound-free) separation, BF cleaning nozzles 6b for carrying out the BF separation, and an agitating mechanism 7 for dispersing the magnetically collected carriers.

In the BF table 6, the magnetically collecting step, the cleaning step and the dispersing step are effected in succession correspondingly to the rotation of the BF table 6. The BF cleaning nozzles 6b have a particular function that prevent the nozzles 6b from entering the reaction vessels or reactors in case of inspection items which need no BF separation.

For the dispersing step described above, it is required that reagents have been previously dispensed in the reaction vessels. Therefore, reagent storing portions A and B are arranged adjacent the BF table 6 so that all the dispensations of reagents take place at the BF table.

In the illustrated embodiment, the BF table 6 is constructed in double lines, that is, outer and inner lines, the former being the dispensing line 6c for the reagent which reacts on a sample, and the latter being the dispensing line 6d of the reagent after the BF separation. With this arrangement, it is possible to perform the dispensations with an improved efficiency. In dispensing a reagent for reacting on a sample having nothing to do with the BF separation, moreover, no magnetic collection mechanism is applied, without collecting magnetic particle carriers, so that the reaction between the sample and the reagent is caused to proceed with high efficiency immediately after the sample dispensation.

It is envisioned that the suction and discharge agitation can be used for the agitating step. In the present invention, however, the agitating system can be employed, in which agitation is carried out by bringing agitating elements into contact with the reaction vessel or reactor.

Figure 11:
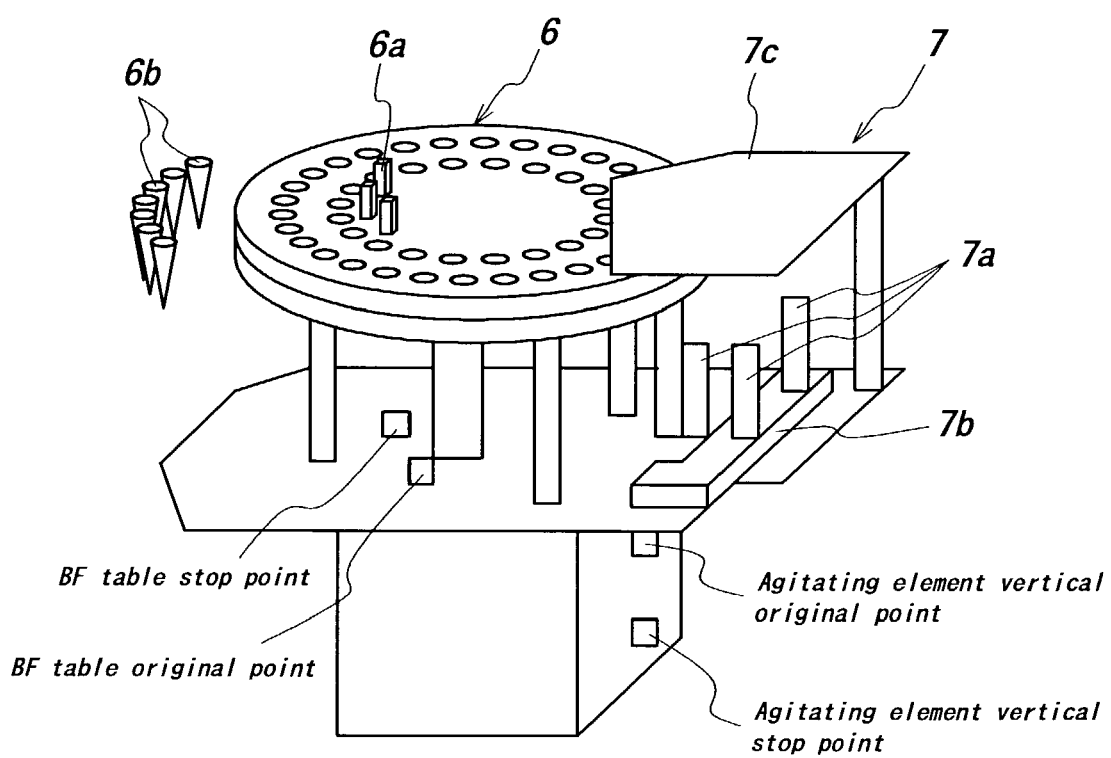
FIG. 11 is a view pictorially illustrating the agitating mechanism of the analyzing apparatus according to the invention.

In the case, for example, that there are a plurality of locations required to be agitated at a time, it is possible to use the agitating mechanism 7 provided with a plurality of agitating elements as shown in FIG. 11. By operating driving source of such an agitating mechanism 7, it is possible to agitate at a plurality of locations at a time.

In FIG. 11, the agitating mechanism 7 comprises agitating elements 7a, a driving source (for example, an electric motor or the like) for rotating the agitating elements 7a, and a restraining member 7c for restraining the reaction vessels c when being agitated.

When the reaction vessels c have been transferred to the location of the magnetically collecting mechanism 6a by means of the rotation of the BF table 6, the magnetic particles in the reaction vessels c are magnetically collected and cleaned in this state by means of the BF nozzles 6. Thereafter, when the reaction vessels c have arrived at the position of the agitating mechanism 7, the contents in the reaction vessels c are agitated by the agitating mechanism 7 so as to permit the magnetic particle carriers in the reaction vessels to be dispersed. The agitating elements 7a are arranged on the driving source 7b which is vertically movable with the aid of a further driving system (not shown).

In agitating, the driving source 7b is moved upward to bring the agitating elements 7a into contact with the bottoms of the reaction vessels c and the restraining member 7c is urged against the upper surfaces of the reaction vessels c so that the reaction vessels c are pinched between the agitating elements 7a and the restraining member 7c. The agitating elements 7a are rotated by the driving source 7b to rock the reaction vessels c, thereby agitating the contents in the reaction vessels. In this case, it is desirable to fix the reaction vessels c by means of the restraining member 7c to prevent the reaction vessels c from irregularly jumping out of their fixed positions and permitting their contents to splash.

With the agitating mechanism 7 described above, it is possible to perform the dispersion of magnetic particle carriers and the mixture of the sample and reagent in the same unit, so that the miniaturization of the apparatus and the reduction in its manufacturing cost can be accomplished.

The apparatus shown in FIGS. 9 and 10 further comprises detecting reaction tables 8 which form a reaction line for producing signals from the immunity composite material combined with the marker substance. The marker substance is for producing signals and may be, for example, an enzyme to which a substrate liquid in a substrate liquid receiving portion K is added to produce the signals.

If the signals are of variation in color, it may be possible to provide a colorimetric detector in the reaction line. In case of using light-emission detection based on the chemical light-emission method, however, because of a need for reducing noise due to stray light as much as possible, there are provided in the reaction line a detecting reaction portion 8a and a detecting measurement portion 8b for detecting the signals. The detecting measurement portion 8b is for detecting weak light-emission produced in the chemical light-emission. In more detail, a photoelectron multiplier tube is used to count the amount of light emission.

In order to obtain a dynamic range for the light-emission measurement, an optical filter is provided at a location of the light-emission measurement portion to measure the light reduced by the filter depending upon the intensity of light-emission, thereby calculating the value of real light-emission from the reduced measured value.

In FIGS. 9 and 10, the apparatus further comprises a sample dispensation transfer portion 9 which is actually a sample dispensing nozzle to which the transfer unit shown in FIG. 1 is applicable. The sample dispensing nozzle serves to collect specimens from racks supplied by a sampler t to dispense them into required reaction vessels. In case of items requiring dilution and pretreatment, for example, the specimens are dispensed into reaction vessels on the outer circumferential line 5a of the immunity reaction table 5, that is, into the reaction vessels on the line for the pretreatment and predilution. In case of a usual analysis not requiring the pretreatment and predilution, the specimens are dispensed into reaction vessels which have reagents previously dispensed at the BF table 6.

The sampler t consists of a rack receiving portion $t_1$ for racks having specimens therein and a rack transfer portion $t_2$ for transferring the racks received in the rack receiving portion $t_1$, in succession to sample dispensing positions. The racks include general specimen racks, quality control racks, measurement line racks, emergency measurement racks, or reinspection racks (racks for second inspection). The sampler t has a function which can distinguish these racks, thereby enabling the apparatus to perform analysis to meet the purposes of the racks. Moreover, the racks can be located at respective exclusive positions, and if required, exclusive racks can be preferentially transferred (for example, when reagent lots have been varied, measurement line racks are preferentially transferred).

In the case that the respective racks have exclusively located positions, they may be preferentially transferred from those positions, and positions at which racks are to be set may be provided in a manner to enable the racks to be newly set. Moreover, a distinguishing function may be provided so that the relevant racks in the sampler t are found out by the distinguishing function and then transferred. Other than the rack distinguishing function, the sampler t has a function that is able to recognize information codes representative of bar codes attached to racks and samples. Analyzing operations may be determined depending upon this function.

The dispensation of samples may be effected by means of fixed nozzles. In consideration of carry-over that is undesirable but occurs in measurement of infection items, disposable sample tips are fitted on distal ends of sample dispensing nozzles to perform dispensation and after use the sample tips are exchanged with new ones.

The sample dispensation transfer portion 9 is designed in a manner to form an operating locus passing through a sample tip supply unit tc, the rack transfer portion $t_2$ of the sampler t, the immunity reaction table 5, and the BF table 6 so that there is no need for preparing a plurality of sample dispensation transfer portions corresponding to inspection items.

The apparatus further comprises a reagent dispensation transfer portion 10 which is actually a reagent dispensing nozzle for collecting reagents from reagent bottles arranged in the reagent storing portions A and B. If required, the transfer unit constructed in a manner shown in FIG. 1 is applicable to the reagent dispensation transfer portion 10.

Reagents are dispensed by the reagent dispensation transfer portion 10 into reaction vessels immediately after they have been cleaned by the BF cleaning at the BF table 6 or into reaction vessels in which samples have not been dispensed.

The reagent dispensation transfer portion 10 is designed in a manner to form an operating locus passing through the reagent storing portions A and B, the BF table 6, and a reaction vessel supply and transfer portion to be described later so that there is no need for preparing a plurality of reaction vessel supply and transfer portions.

According to the exemplary embodiment of the invention, in order to develop the treating speed, the number of the units of the reagent dispensation transfer portion 10 is two, that is, reagent dispensation transfer portions 10a and 10b so that it is possible to receive and dispense the reagents at a plurality of locations.

The BF cleaning nozzle 6b is for sucking the inspection liquids or BF liquids and supplying BF liquids and is formed by a suction nozzle and a delivery nozzle forming one set of BF cleaning nozzles.

In FIGS. 9 and 10, the apparatus further comprises a reaction vessel transfer portion 11 for transferring the reaction vessels c between the respective tables and further transferring the reaction vessels c to a reaction vessel supply portion U, the detecting reaction portion 8a, and a reaction vessel disposing portion L.

The reaction vessel transfer portion 11 may be constructed by vessel gripping means. However, the transfer unit as shown in FIG. 1 may be applicable to the reaction vessel transfer portion 11. With such a transfer unit, different from the vessel gripping means, one mechanism can be dispensed with, thereby enabling reduction in manufacturing cost and improvement of reliability.

The reagent storing portions A and B are kept at constant temperatures and may be arranged on the operating locus of reagent dispensation transfer portion 10 or on the same operating locus as turn tables.

In order to increase the number of settled reagents, according to the exemplary embodiment of the invention there are provided two reagent storing portions constructed as turn tables, and the reagent storing portions A and B are arranged on the operating locus of the reagent dispensation transfer portion 10, thereby enabling a single transfer portion to dispense reagents contained in a plurality of reagent storing portions.

In case of preparing two reagent storing portions for magnetic particle solidus carrier reagent liquid and for marker reagent, by providing such two reagent storing portions, where the respective reagents should be set can be clearly distinguishable. With this arrangement, moreover, it may be possible to vary shapes of reagent bottles depending upon the kinds of reagents to limit the places where the reagents are set by providing shaped portions to meet the shapes of the bottles.

The numbers of reagents permitted in the respective reagent storing portions may be not necessarily the same. Bearing in mind that the pretreatment liquids or dilute solutions are set in either of the reagent storing portions, for example, more of the reagents may be set in one of the reagent storing portions.

In the event that the reagents to be set in the reagent storing portions are, for example, magnetic particle solidus carrier reagents, the magnetic particles will settle out as the time elapsed to cause a concentration gradient, resulting in incorrect data.

In order to prevent such incorrect data, the reagents are agitated in the reagent dispensation transfer portion 10 before the dispensation of the reagents. For example, the liquids are agitated by suction and discharge agitation, or the magnetic particles are dispersed with the aid of an ultrasonic vibratory element provided on the nozzle.

For such a purpose, it is preferable to provide an agitating mechanism at the reagent storing portion for dispersing the magnetic particles. With this arrangement, the reagent previously received in a cylindrical bottle is subjected to rotation about an axis of the bottle so as to permit the magnetic particles to disperse with the aid of frictional force between the liquid and the wall surface of the bottle. Such rotation about the axis may be accomplished in connection with the rotation of the turn table so that a driving mechanism for the rotation of the bottle about its axis can be dispensed with.

In the case using the magnetic particle solidus carrier reagents as reagents, according to the invention it is possible to gather these reagents together in one reagent storing portion so that the agitating mechanism described above is needed only in one receiving portion to serve to reduce the manufacturing cost.

The agitating mechanism should not be limited to that described above. If the reagent storing portion is a turn table, for example, the turn table may be rotated at a high speed for utilizing the centrifugal force, or agitating elements are brought into abutment against the bottle to agitate the regent in the bottle.

A bottle of the reagent has a reagent code (for example, bar code) attached thereto recording the information of the reagent (for example, a lot, effective term, measurement line information or the like). The reagent storing portion is provided with means for reading these codes (for example, a bar code reader, image reader, magnetic reader or the like) so that the information read from the information code together with positional information of the reagent storing portion which has been set, its set date and the like is transmitted to a data processor and memorized.

The substrate receiving portion (substrate dispensing unit) K may be arranged in the proximity of the reagent storing portions A and B. In the present invention in consideration of the need for a large amount of reagent because the substrate is a common reagent, separate substrate receiving portions are preferably provided to dispense the reagent at exclusive dispensing units.

In reality, a plurality of bottles for receiving the substrate are made to be set simultaneously and the dispensation is effected by the line dispensing system. At this time, even if bottles concerning different lots are set, it is preferable to selectively dispense the reagent from the respective bottles, thereby enabling the dispensation from the needed bottles.

The sample tip supply unit tc is provided on the apparatus with a tip case having a plurality of aligned tips, from which tip case the chips are supplied. In reality, the tip case may be moved to the tip supply positions, or tip transfer means may be used to transfer the tips from the tip case to the supply positions for supplying the tips. The tip case is longitudinally received so as to occupy a minimum possible space to miniaturize the apparatus.

Similarly to the sample tip supply unit tc, with the reaction vessel supply unit J, empty vessels aligned on a box are arranged on the apparatus to transfer the box to the position of reaction vessel supply portion U. In consideration of addition of reactor vessels at any time and miniaturization of the apparatus, it is preferable to provide feeders for parts in the apparatus so that the feeders are aligned at the position of the reaction vessel supply portion U.

An analyzing method for automatic analysis using two step method with the apparatus shown in FIG. 9 will be explained hereinafter. Reaction vessels c are supplied from the reaction vessel supply unit J and set on the reaction vessel supply portion U by means of the reaction vessel transfer portion 12. The reaction vessels c set on the reaction vessel supply portion U are then transferred to the BF table (outside) 6 by the reaction vessel transfer portion 1, and thereafter the magnetic particle solidus carrier reagent is dispensed into the reaction vessels by the reagent dispensation transfer portion (dispensing nozzles) 10.

Samples are collected from the specimen racks supplied by the sampler t by means of the sample dispensation transfer portion 9 having disposable sample tips mounted thereon and are dispensed into reaction vessels c on the cleaning table. The contents in the reaction vessels c are then agitated by the agitating mechanism 7 of the BF table 6 and thereafter the reaction vessels c are transferred to the intermediate circumferential line 5b of the immunity reaction table 5 by means of the reaction vessel transfer portion 11.

After the lapse of a predetermined reaction time, the reaction vessels c are further transferred to the BF table (inside) 6 by means of the reaction vessel transfer portion 11, and the magnetic particle carriers in the reaction vessels are magnetically collected by means of the magnetically collecting mechanism 6a set on the BF table 6 and are subjected to the BF separation by the BF cleaning nozzles 6b.

After the BF separation, the marker reagents are dispensed from the reagent storing portion A into the reaction vessels c by means of the reagent dispensation transfer portion 10, and the contents in the reaction vessels are agitated by the agitating mechanism 7. After the agitation, the reaction vessels c are transferred to the inner circumferential line 5c of the immunity reaction table 5 by means of the reaction vessel transfer portion 11, and after the lapse of a predetermined reaction time, the reaction vessels c are transferred to the BF table (inside) 6 by means of the reaction vessel transfer portion 11.

The magnetic particle carriers in the reaction vessels c are further magnetically collected by means of the magnetically collecting mechanism 6a and are subject to the BF separation by the BF cleaning nozzles 6b. After the BF separation, the substrate liquids in the substrate receiving portion K are dispensed into the reaction vessels by means of the substrate liquid dispensing unit.

After the dispensation of the substrate liquids, the contents in the reaction vessels are further agitated by the agitating mechanism 7, and thereafter the reaction vessels are once located at the detecting reaction portion 8a of the detecting reaction table 8 by the reaction vessel transfer portion 11. After the lapse of a predetermined reaction time, the reaction vessels are transferred to the detection measurement portion 8b by means of the reaction vessel transfer portion 12, where the light emitted from the reaction vessels c is measured by the use of the photoelectron multiplier tube to determine the existence of the object substance in the specimen to be inspected. In this case, the transfer unit shown in FIG. 1 is applicable to the reaction vessel transfer portion 12.

After the measurement described above, the reaction vessels c are transferred to the reaction vessel disposing position L by means of the reaction vessel transfer portion 12 and are disposed or thrown away.

The automatic analysis using one step method will be carried out in the following manner. First, the reaction vessels c are set in the reaction vessel support portion U by means of the reaction vessel transfer portion 12 and further transferred to the BF table (outside) 6 by means of the reaction vessel transfer portion 11.

The magnetic particle solidus carrier reagents and marker reagents are dispensed into the reaction vessels c transferred to the BF table 6 by means of the reagent dispensation transfer portion 10. Samples are collected from the specimen racks supplied from the sampler t by means of the sample dispensation transfer portion 9 having sample tips fitted thereon and are dispensed into the reaction vessels c on the BF table 6.

After the contents in the reaction tables c are agitated by the agitating mechanism 7, the reaction vessels c are transferred to the intermediate circumferential line 5b of the immunity reaction table 5 by means of the reaction vessel transfer portion 11, and after the lapse of a predetermined reaction time in the line 5b, the reaction vessels are transferred to the BF table (inside) 6 by means of the reaction vessel transfer portion 11.

The reaction vessels c described above set on the BF table 6 are subjected to the BF cleaning process and at that time, the BF cleaning nozzles 6b are controlled so as not to be transferred into the reaction vessels c so that the BF separation does not take place.

It can be thought that the reaction vessels c may be affected by the influence of the magnetic collecting mechanism 6a. Similarly to the two step method, the contents in the reaction vessels are agitated by the agitating mechanism 7 on the BF table 6, and the reaction vessels are then transferred to the inner circumferential line 5c of the immunity reaction table 5 by means of the reaction vessel transfer portion 11. Thereafter, the same steps as those in the two step method are carried out to determine the existence of the object substances.

Moreover, the present invention can perform an analysis in a manner to combine the one and two step methods. For example, the invention is applicable to a reaction system in that a sample and a marker reagent are caused to react on each other and magnetic particle carrier reagent is dispensed into a reaction vessel without carrying out the BF separation (delay one step method).

The automatic analysis using two step method including dilution and pretreatment is performed in the following manner. Reaction vessels c (for dilution and pretreatment) supplied from the reaction vessel supply unit J are set at, for example, the position L as a supply portion for pretreatment. For the items requiring the dilution or pretreatment, the dilute solution or pretreatment liquid set in, for example, the reagent storing portion B is dispensed into the reaction vessels c by means of the reagent dispensation transfer portion 10, and thereafter the reaction vessels are transferred to the outer circumferential line 5a of the immunity reaction table 5 by means of the reaction vessel transfer portion 11.

Samples are collected from the specimen racks supplied from the sampler t by means of the sample dispensation transfer portion 9 having sample tips fitted thereon, and such samples are dispensed into the reaction vessels c on the immunity reaction table 5.

During the steps described above, another reaction vessel c (for measurement) is set in the reaction vessel supply portion U and is transferred to the BF table (outside) 6 by means of the reaction vessel transfer portion 11. The magnetic particle solidus carrier reagent is dispensed into the reaction vessel (for measurement) transferred to the BF table 6 by means of the reagent dispensation transfer portion 10. (The one step method and other measuring method are substantially similar to those described above.)

Samples are collected from the reaction vessels (for dilution and pretreatment) containing samples diluted and pretreated by means of the sample dispensation transfer portion 9, and such samples are dispensed into the reaction vessels (for measurement) on the BF table and the contents in the reaction vessels are then agitated by the agitating mechanism 7. The following analyzing operations for the reaction vessels (for measurement) are carried out in the similar manner to those in the two step method described above (or another method described above). The reaction vessels (c for dilution and pretreatment) are transferred to the reaction vessel disposing position L and disposed or thrown away.

Although the automatic analysis using two reactor vessels is explained in the above embodiment, it is possible to perform the automatic analysis including dilution and pretreatment using only one reaction vessel. For this purpose, first, a reaction vessel (for dilution and pretreatment) c, which has been subjected to a dilution or pretreatment, is transferred from the immunity reaction table 5 to the BF table 6, and thereafter the reaction vessel c is subjected to the same steps as those in the reaction vessel c for measurement described above with the exception of the dispensation of the sample on the BF table 6. In this manner, it is possible to perform the dilution and pretreatment with only one reaction vessel.

In order to carry out the analysis continuously for a prolonged period of time, preferably there may be provided means capable of setting a plurality of substrate bottles or means capable of supplying reaction vessels with a feeder for parts. In this case, there are further provided a plurality of tip cases having sample tips received therein and means for transferring tips from the tip cases to tip supply portion positions (where nozzles and tips are fitted with each other), such that the transportation of tip cases themselves is reduced as much as possible or eliminated, thereby enabling used tip cases to be conveniently and safely exchanged with new tip cases even in analyses continuing for a prolonged period of time.

By providing the feeder for parts, it becomes possible to add consumption articles at any time without stoppage of the apparatus. It is common to prepare an exclusive cleaning agent for nozzles. Preferably, a cleaning agent reservoir is provided, which is able to automatically dilute a concentrated cleaning agent to supply the dilute cleaning agent, thereby enabling the concentrated cleaning agent to be replenished.

Used consumption articles to be discarded are transferred by a discarding box. When the discarding box is filled with the articles to be discarded, the box is exchanged with a subsidiary tank, thereby enabling waste articles to throw away at any time. Moreover, a pump is provided to automatically discharge the waste liquor, thereby enabling continuous treatment of the waste liquor.

In the analyzing operations described above, it is assumed that the immunity reaction time or pretreatment reaction time is terminated during one rotation of the immunity reaction table 5. However, the liquid to be inspected is maintained until the immunity reaction table 5 has been rotated a plural times depending upon the performance or property of a reagent so as to permit the reaction time (including pretreatment time) to be prolonged for the number of rotations. Therefore, it becomes possible to use a reagent whose reaction time is comparatively long.

Each of tables is controlled to be at a constant temperature in a manner that the immunity reaction and the reaction for producing signals are effected under the most suitable conditions. For this purpose, each of the tables is made of a substance superior in thermal conductivity, for example, aluminum and is heated directly by heating means such as a heater or is brought into contact with another heat source. The temperature of the table is controlled at a constant by monitoring by the use of a thermistor.

In addition to the tables, the reaction vessel supply portion and the detection measurement portion may be controlled to be constant temperatures. In order to avoid any variance in temperature of liquids to be inspected during cleaning (BF operation) of the reaction vessel, the BF nozzle 6b may be controlled to be a constant temperature or the BF liquid may be supplied after being heated by causing it to pass through a heated portion.

In order to avoid any variance in temperature of liquids to be inspected during dispensing operation of the reagent, preferably, the reagent dispensation transfer portion 10 is controlled to be a constant temperature, or the cleaning agent for cleaning the nozzles is supplied after it has been warmed up by previously causing it to pass through a heated portion.

The operating conditions of the respective tables may be determined so as to be the most suitable conditions in layout to meet specifications of automatic analysis to be effected. For example, the table may be moved with one pitch or 180° plus one pitch per one cycle of operation. In effect, the table may be operated with a cycle commensurate with the number of ports at which reaction vessels can be set such that all the ports can be used. The respective operations of the tables may be suitably set without requiring any coincidence of operating conditions of the respective tables.

Figure 12:
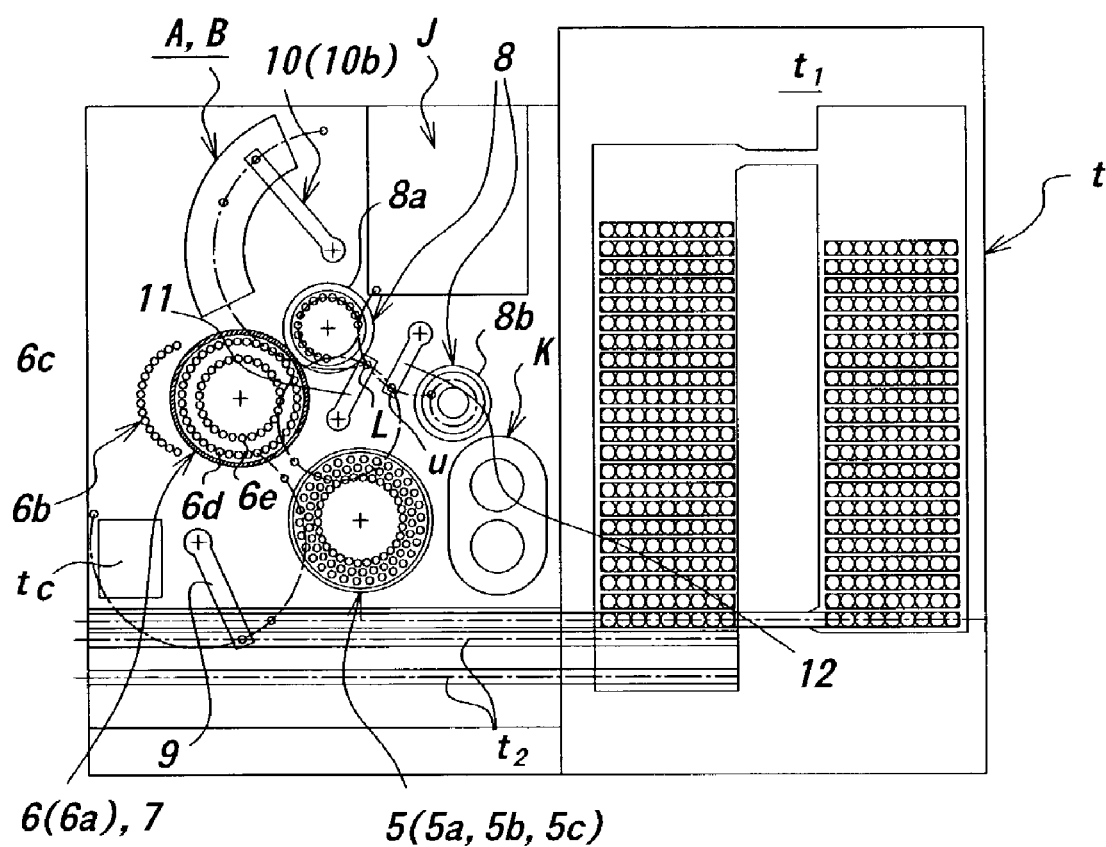
FIG. 12 is a view illustrating an automatic analyzing apparatus according to another embodiment of the invention.

FIG. 12 illustrates an analyzing apparatus having one reagent storing portion according to another embodiment of the invention. With this apparatus of the construction, the reagent storing portion may be stationary and in the form of a turn table, and the portion 10a of the reagent dispensation transfer portion 10 shown in FIG. 10 can be omitted. In this case, the apparatus can be more miniaturized.

Figure 13:
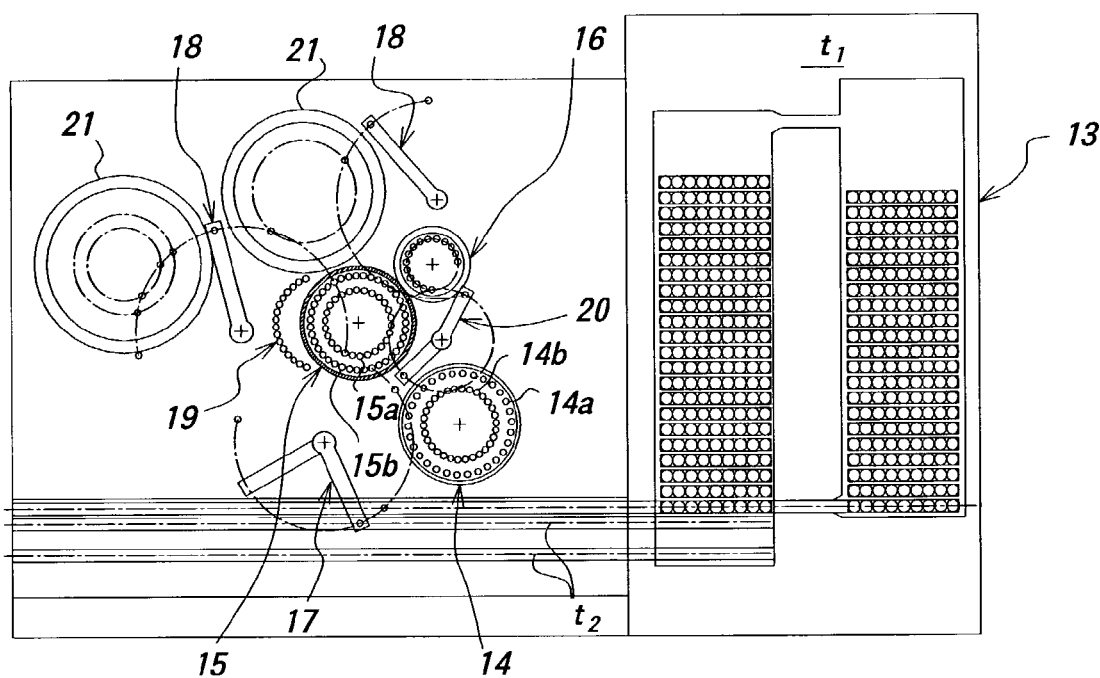
FIG. 13 is a view illustrating an automatic analyzing apparatus according to a further embodiment of the invention.
Figure 14:
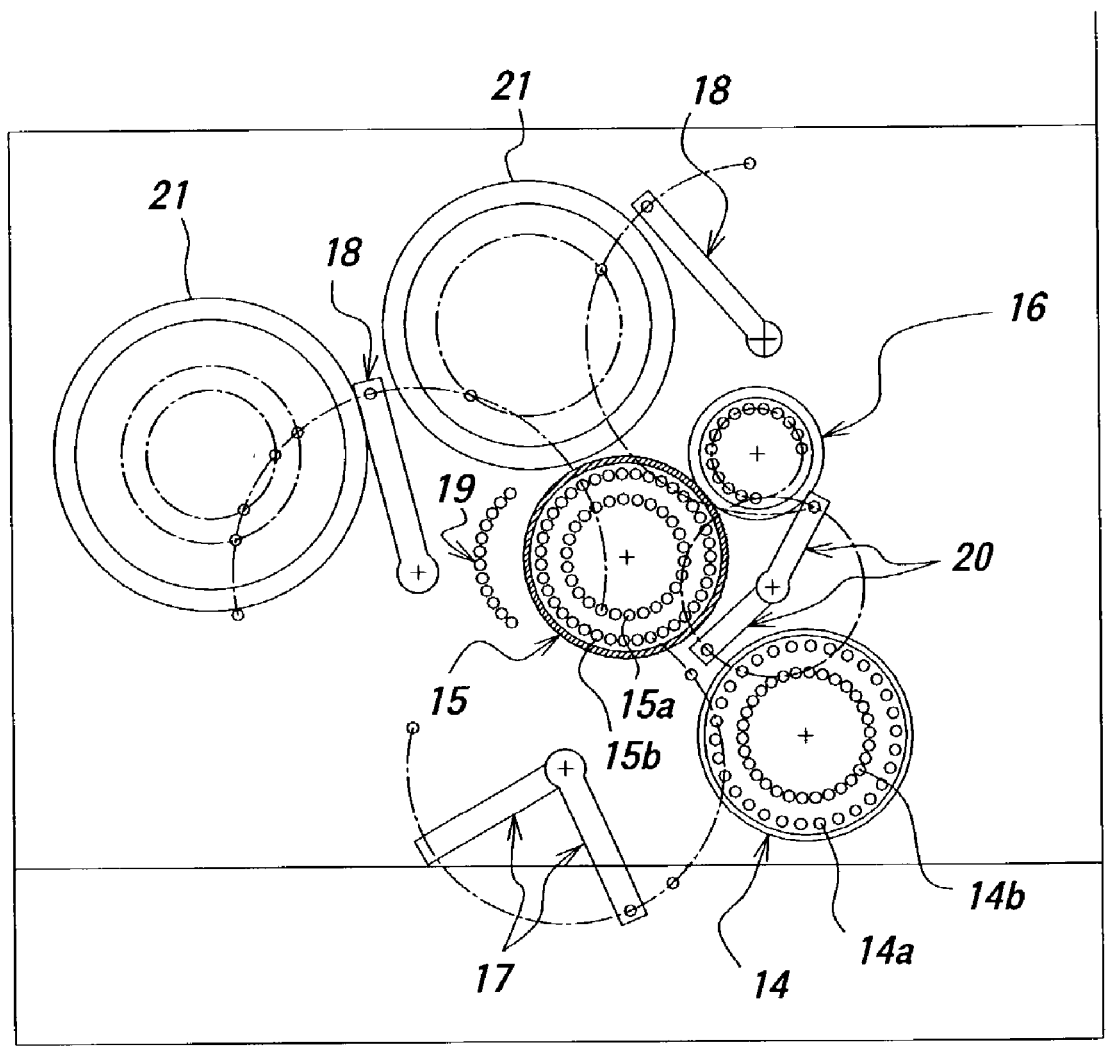
FIG. 14 is a view showing an important portion of the apparatus shown in FIG. 13.

FIGS. 13 and 14 illustrate the entire construction and an important portion of an automatic analyzing apparatus according to another embodiment of the invention applied to measurement for chemicobiological and homogeneous immunity items.

In FIGS. 13 and 14, the apparatus comprises a sampler 13, a reaction table 14, a cleaning table 15, a detecting reaction table 16, a sample dispensing nozzle 17, reagent dispensing nozzles 18, a reaction vessel cleaning nozzle 19, a reaction vessel transfer portion 20, and a reagent storing portion 21. In the analyzing apparatus constructed described above, the sampler 13 may be similar to the sampler t shown in FIG. 9.

The reaction table 14 may have a reaction line having a configuration of a double construction consisting of an outer circumferential line 14a for pretreatment and predilution and an inner circumferential line 14b for reaction of sample and first reagent.

The cleaning table 15 has cleaning nozzles for cleaning reaction vessels after completion of measurement, and all the dispensations of reagent take place in the cleaning table 15. The cleaning table 15 includes double lines, that is, on inner side a reaction vessel cleaning line 15a and on outer side a reagent dispensing line 15b, thereby enabling the dispensing steps to be effected with high efficiency. The reaction vessel cleaning line 15a of the cleaning table 15 may be provided with reaction vessel locating positions a few times (about three times in the drawing) the reaction vessel locating positions of the dispensing line 15b so that the reaction vessels including reaction vessels for dilution can be cleaned at the cleaning line 15a.

The suction and discharge agitation can be carried out by the use of the dispensing nozzles. According to the invention, however, it is preferable to employ the agitating mechanism similar to that shown in FIG. 11. The detecting reaction table 16 is provided on its reaction line with a calorimetric detector to accommodate both the rate method and end method.

The sample dispensing nozzle 17 collects specimens from the racks supplied by the sampler 13 and dispenses the specimens into required reaction vessels. In case of items requiring dilution and pretreatment, for example, the specimens are dispensed by the sample dispensing nozzle 17 into reaction vessels on the pretreatment and predilution lines of the reaction table 14. In a normal analysis, as described above, in the cleaning table 15 the dispensation is effected into the reaction vessels into which reagents have previously been dispensed. The sample dispensing nozzle 17 is designed to have an operating locus passing through the rack transfer portion $t_2$ of the sampler 13, the reaction table 14 and a cleaning table 15. A plurality of the sample dispensing nozzles 17 are not necessarily needed according to inspection items.

The reagent dispensing nozzles 18 collect reagents from the reagent bottles arranged in the reagent storing portion 21 and dispense the reagent into required reaction vessels or into reaction vessels into which samples have not been dispensed. The reagent dispensing nozzles 18 are designed to have an operating locus passing through the reagent storing portion 21 and the cleaning table 15.

The two units of the reagent dispensing nozzle 18 are shown in the illustrated embodiment. By increasing the number of units of the nozzle 18, the collection and dispensation can be effected at a plurality of positions from the reagent storing portion 21, thereby considerably increasing the treating speed.

The reaction vessel cleaning nozzle 19 performs suction of liquids to be inspected and supply of cleaning agent and consists of a combination of a suction nozzle and a discharge nozzle. Concerning the reaction vessel transfer portion 20, the transfer unit shown in FIG. 1 may be used for the same purpose.

The reagent storing portion 21 is maintained at a constant temperature and may be in the form of a turn table arranged in coincidence with the operating locus of the reagent dispensing nozzle 18 as shown in FIG. 9 or may be arranged side by side on the operating locus of the reagent dispensing nozzles 18 as shown in FIG. 12. A plurality (two in the illustrated embodiment) of reagent storing portions 21 in the form of a turn table are arranged so that it becomes possible to dispense reagents arranged in a plurality of reagent storing portions by means of a single reagent dispensing nozzle 18.

A bottle of the reagent in the reagent storing portion 21 has a reagent code (for example, bar code) attached thereto recording the information of the reagent (for example, a lot, effective term, measurement line information or the like). The reagent storing portion 21 is provided with means for reading these codes, such as a bar code reader, image reader, magnetic reader or the like so that the information read from the information code together with positional information of the reagent storing portion 16 which has been set, set date and the like is transmitted to a data processor and memorized.

The automatic analysis using the apparatus shown in FIGS. 13 and 14 is carried out in the following manner. First, a reaction vessel is cleaned in the inner line of the cleaning table 15 and a first reagent is dispensed into the reaction vessel by means of the reagent dispensing nozzle 18. Thereafter, a sample is dispensed into the reaction vessel by means of the sample dispensing nozzle 17, and the content in the reaction vessel is agitated by an agitating mechanism in successive manner.

After agitation, the reaction vessel is transferred to the inner line of the reaction table 14 by means of the reaction vessel transfer portion 20. The reaction vessel is kept at this location for a constant reaction time and then transferred to the outer line of the cleaning table 15 by means of the reaction vessel transfer portion 20. If required, a second reagent and a third reagent are dispensed into the reaction vessel on the cleaning table 15 and then the content in the reaction vessel is agitated.

Thereafter, the reaction vessel is moved to the detecting reaction table 16 by means of the reaction vessel transfer portion 20, where the reaction condition of the content in the reaction vessel is detected by the rate method or end method using a colorimeter. After the detection, the reaction vessel is transferred to the inner circumferential line of the cleaning table 15 by means of the reaction vessel transfer portion 20 and cleaned.

The analysis requiring dilution and pretreatment is carried out in the following manner. When a first reagent is dispensed into a cleaned reaction vessel, simultaneously a dilute solution or pretreatment liquid set in the reagent storing portion 21 is dispensed into the reaction vessel by means of the reagent dispensing nozzle 18, and then a sample is dispensed into the reaction vessel by means of the sample dispensing nozzle 17. Thereafter, the content in the reaction vessel is agitated by the agitating mechanism.

After the agitation, the reaction vessel is transferred to the outer circumferential line 14a of the reaction table 14 by means of the reaction vessel transfer portion 20. When the reaction vessel whose content has been subjected to the dilution or pretreatment is transferred onto the operating locus of the sample dispensing nozzle 17, a reaction vessel for test reaction is assigned to the reaction vessel in a manner such that a sample liquid which has been diluted or pretreated can be dispensed into the reaction vessel at the sample dispersion timing in normal operation.

The vessel assigned as a reaction vessel is transferred to the inner circumferential line of the cleaning table 15 where the vessel is cleaned and a first reagent is dispensed into the vessel. Thereafter, a sample liquid that has been diluted or pretreated is dispersed at the sample dispersing timing into the vessel from the reaction vessel (whose content has been diluted or pretreated) arranged on the outer circumferential line of the reaction table 14.

Thereafter, the reaction vessel is subjected to the steps the same as those in the normal operation. The reaction vessel used for dilution or pretreatment is returned to the cleaning table 15 by means of the reaction vessel transfer portion 20 to be cleaned.

FIGS. 13 and 14 illustrate the apparatus for measuring and analyzing chemicobiological items, which, however, is included in the apparatus shown in FIGS. 9 and 10 for measuring and analyzing the immunity items. With the apparatus shown in FIGS. 9 and 10, by suitably controlling the transferring of the reaction vessels, both the chemicobiological (homogeneous) items and immunity (heterogeneous) items can be analyzed or measured only by one apparatus. The present invention should not be limited to these apparatuses.

While the invention has been particularly shown and described with reference to preferred embodiments thereof, it will be understood by those skilled in the art that the foregoing and other changes in form and details can be made therein without departing from the spirit and scope of the invention.

What is claimed is:

1. A transfer unit comprising:
   at least one holder which transfers members to proceed a reaction in an automatic analyzer;
   said holder having a rod portion and a guide portion, one of which can slide relatively to the other elastically to release said member from the distal end of said rod portion;
   wherein said guide portion has at least one elongated aperture and said rod portion has a protrusion corresponding to said elongated aperture and is movable within said elongated aperture, said protrusion extending through said elongated aperture of said guide portion such that contact of said protrusion with a fixed member causes said protrusion to move within said elongated aperture and further causes relative movement between the rod portion and guide portion to release said member.

2. The transfer unit as set forth in claim 1, wherein said rod portion has at least one window at the top of the rod for detecting a mounting and dismounting of said member onto and from said rod portion.

3. The transfer unit as set forth in claim 1, wherein said members are reaction vessels.

4. The transfer unit as set forth in claim 1, wherein said members are dispersing tips.

5. An automatic analyzing apparatus comprising;
   a reaction portion for causing a reaction of a substance and a reagent mixed into a liquid,
   a detecting portion for signal or reaction from the liquid,
   a washing portion for removing an unreacted substance in the reacted liquids,
   a transfer unit to transfer members to proceed a reaction;
   wherein said transfer unit has at least one holder which transfers members to proceed a reaction in an automatic analyzer, said holder having a rod portion and a guide portion, one of which can slide relatively to the other elastically to release said member from the distal end of said rod portion, said guide portion has at least one elongated aperture and said rod portion has a protrusion corresponding to said elongated aperture and is movable within said elongated aperture, said protrusion extending through said elongated aperture of said guide portion such that contact of said protrusion with a fixed member causes said protrusion to move within said elongated aperture and further causes relative movement between the rod portion and guide portion to release said member.

6. The automatic analyzing apparatus as set forth in claim 5, wherein said rod portion has at least one window at the top of the rod portion for detecting a mounting and dismounting of said member onto and from said rod portion.

7. The automatic analyzing apparatus as set forth in claim 5, wherein said members are reaction vessels.

8. The automatic analyzing apparatus as set forth in claim 5, wherein said members are dispensing tips.

9. The automatic analyzing apparatus as set forth in claim 5, wherein said washing portion works for B/F separation.

10. Means for transferring members in an automatic analyzer comprising:
    a member holding means wherein said members are detached by sliding a rod portion or a guide portion relatively to the other elastically to release said member from the distal end of said rod portion, wherein said guide portion has at least one elongated aperture and said rod portion has a protrusion corresponding to said elongated aperture and is movable within said elongated aperture, said protrusion extending through said elongated aperture of said guide portion such that contact of said protrusion with a fixed member causes said protrusion to move within said elongated aperture and further causes relative movement between the rod portion and guide portion to release said member.

11. The means as set forth in claim 10, wherein said rod portion has at least one window at the top of the rod for detecting a mounting and dismounting of said member onto and from said rod portion.

12. The means as set forth in claim 10, wherein said members are reaction vessels.

13. The means as set forth in claim 10, wherein said members are dispensing tips.

* * * * *